United States Patent [19]
Fritzsch

[11] Patent Number: 5,971,994
[45] Date of Patent: Oct. 26, 1999

[54] HIGH FREQUENCY SURGICAL INSTRUMENT

[75] Inventor: Gernod Fritzsch, Tuttlingen, Germany

[73] Assignee: Gebrueder Berchtold GmbH, Tuttlingen, Germany

[21] Appl. No.: 09/115,399

[22] Filed: Jul. 14, 1998

[30] Foreign Application Priority Data

Jul. 16, 1997 [DE] Germany ............ 197 30 525

[51] Int. Cl.⁶ .................................. A61B 17/24
[52] U.S. Cl. .............. 606/113; 606/114; 606/115; 606/127; 606/128; 606/46; 606/47
[58] Field of Search .............. 606/110–115, 46, 606/47, 48, 1, 79, 127, 128, 200

[56] References Cited

U.S. PATENT DOCUMENTS

| 2,856,933 | 1/1958 | Hildebrand et al. ............ 128/305 |
| 3,955,578 | 5/1976 | Chamness . |
| 4,718,419 | 1/1988 | Okada ..................... 128/303.15 |
| 5,207,686 | 5/1993 | Dolgin . |
| 5,437,665 | 8/1995 | Munro ........................ 606/47 |

FOREIGN PATENT DOCUMENTS

| 690697 | 9/1940 | Germany . |
| 7407057U1 | 8/1974 | Germany . |
| 2132808 | 8/1977 | Germany . |
| 7835595 | 1/1978 | Germany ............... 606/113 |
| 7835595U1 | 4/1979 | Germany . |
| 3626371A1 | 2/1987 | Germany . |
| 4100422A1 | 7/1992 | Germany . |
| 69110794T2 | 12/1995 | Germany . |

OTHER PUBLICATIONS

Rockhlin, Device for electrical excision of gastric polyps throuhg a gastroscope, Biomedical Engineering, vol. 8, No. 2, p. 118–119, Jan. 1975.

*Primary Examiner*—Michael Buiz
*Assistant Examiner*—Wen Ngo
*Attorney, Agent, or Firm*—Townsend and Townsend and Crew LLP

[57] ABSTRACT

The invention relates to a high frequency surgical instrument comprising a handling part (11) which has a guide channel (12) which is open at at least one end and a holding element (13) which is axially displaceably guided therein and on which a high frequency voltage acts. The holding element (13) is axially displaceable by means of an actuating part (14) axially displaceable relative to the handling part (11) and is electrically conductively connected at its free end to a preferably elastic cutting loop (15) in such a way that, through axial adjustment of the actuating part (14), the cutting loop (15) can be drawn to a greater or lesser degree into the guide channel (12), or into a tube (16) which continues it outwardly, or can be pushed out of the guide channel (12), or out of the tube (16) continuing it outwardly, whereby the loop size can be changed. The design is such that the two limbs (15', 15") of the cutting loop (15) are releasably secured to a shaft (13) which is guided in the guide channel (12) or tube (16) and forms the holding element.

21 Claims, 2 Drawing Sheets

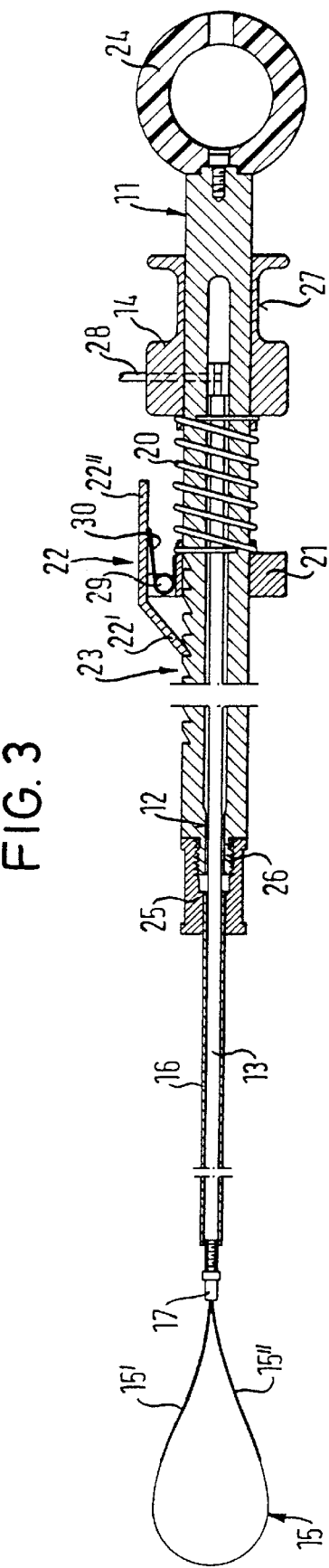
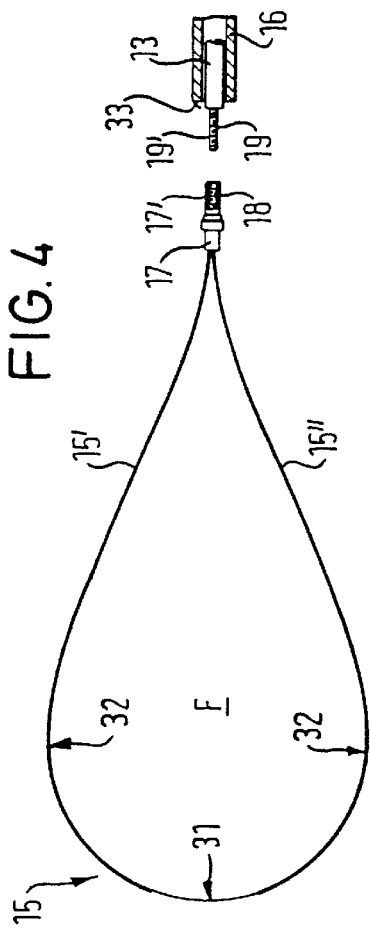
FIG. 3
FIG. 4

HIGH FREQUENCY SURGICAL INSTRUMENT

The invention relates to a high frequency surgical instrument comprising a handling part which has a guide channel which is open at at least one end and a holding element which is axially displaceably guided therein and on which a high frequency voltage acts, with the holding element being axially displaceable by means of an actuating part axially displaceable relative to the handling part and being electrically conductively connected at its free end to a preferably elastic cutting loop in such a way that, through axial adjustment of the actuating part, the cutting loop can be drawn to a greater or lesser degree into the guide channel, or into a tube which continues it outwardly, or can be pushed out of the guide channel or out of the tube continuing it outwardly, whereby the loop size can be changed.

Such high frequency surgical instruments are used together with high frequency surgical apparatus in order to cut biological tissue with little escape of blood, to remove proliferating tissues or deceased parts of the body and for other purposes. High frequency surgical instruments of the initially named kind are already known in which monopolar or unipolar cutting loops can be made larger or smaller by the displacement of the actuating part relative to the handling part (German Utility Model 78 15 921; U.S. Pat. No. 5,201,741).

Since it is frequently necessary to work with high frequency surgical apparatus using higher levels of high frequency power, and since the unipolar wire loops are generally very thin, the working life of the cutting loops is restricted so that it may only suffice to carry out a single operation. In such high frequency surgical instruments the exchanging of damaged or destroyed cutting loops is very complicated because the instruments must be partly fully dismantled in order to exchange the stroke rods forming the actuating part together with the cutting loops.

A further problem in known high frequency surgical instruments with cutting loops lies in the fact that, once a cutting loop size is set, it can only be kept constant by special attention of the surgeon. Moreover, in such instruments, the cutting loop must be kept under a certain pre-stress, by the hand force or finger force exerted by the operator at the grip, so that it does not slip.

The object of the invention is to design a high frequency surgical apparatus of the initially named kind that makes the exchanging of worn out or broken cutting loops possible, quickly and without problem.

BRIEF SUMMARY OF THE INVENTION

In order to satisfy this object there is provided, in accordance with the present invention, a high frequency surgical instrument of the initially named kind which is characterized in that the two limbs of the cutting loop are releasably secured to a shaft which is guided in the guide channel or tube and forms the holding element.

Advantageous instruments in accordance with the invention are characterized by the fact that the limbs are led to a common base, which is in turn releasably connectable to the shaft and is so dimensioned that it is displaceable with the shaft within the guide channel and/or within the tube.

It is furthermore characterized in that the base is releasably connected to the shaft via a threaded connection and in that the base is connectable to the shaft via a bayonet connection.

A further advantageous instrument in accordance with the invention is characterized in that the shaft can be displaced forwardly in the guide channel and/or in the tube to such an extent that its front connecting end is located at least so close to the front end of the guide channel or tube respectively, and preferably projects out of this end, that the limbs of the cutting loop or the base can be released from the connection end or connected to it without problem.

The concept of the invention is thus to be seen in the fact that one forms the cutting loop, in particular through the connection with a base, as a component which can be separated from the remainder of the instrument, so that to exchange a cutting loop one does not have to dismantle the entire instrument, but rather it is only necessary to use simple manual actions, such as unscrewing or unlatching a bayonet connection, to remove the cutting loop and to replace it by a new cutting loop of the same design.

A first advantageous practical embodiment of particularly simple construction is characterized by the fact that that the actuating part is arranged behind the handling part. The guide channel passes up to the rear end of the handling part and the shaft extends through the rear end of the guide channel to the actuating part and is fixedly connected to the latter. The shaft extends into the actuating part and is electrically conductively connected from there to a high frequency contact, in particular to a high frequency plug contact which can be connected from the outside to a counterpiece coming from the high frequency generator. The actuating part contacts the rear end of the handling part when the cutting loop is open to the greatest degree.

A further embodiment which is particularly compact in the axial direction is characterized in that the actuating part is formed as an actuating ring which is axially slidably arranged on the handling part and is connected through an elongate slot to the shaft which is axially guided inside of the handling part.

A particularly secure grasping of the actuating part is ensured by a further development of an instrument in which the actuating part has a gripping depression which preferably extends around it.

The embodiment of an instrument in which the actuating part is biased by a spring arrangement in the direction of a reduction of the loop makes it possible to apply the force for contracting the cutting loop at the desired level through the spring arrangement, so that the surgeon only has to control the actuating part and is less obliged to apply force to it.

The embodiment of an instrument in which a fixing means is provided for the cutting loop when drawn into a specific position is expedient in order to retain the cutting loop which has been drawn together to a greater or lesser degree in a specific position that has been reached.

In particular, use should be made of a fixing device which comprises a fixing apparatus which blocks at one side and which is correspondingly co-displaced on reduction of the size of the cutting loop but is only displaceable in the sense of an increase in the size of an cutting loop through a hand actuated deblocking device.

The contraction of the loop can then take place when the fixing device is not active and the fixation then follows after achieving the desired end position of the cutting loop.

One can find particularly advantageous practical embodiments in instruments in which the spring arrangement is disposed between the fixing means and the actuating part. Such instruments are further characterized in that the fixing means comprises a fixation which is displaceably guided on the handling part and which is loaded by a spring in the blocking direction, a latch pawl arranged on the fixation and an axial latch tooth arrangement on the handling part. A coil spring is arranged between the fixing ring and the actuating part. The handling part is at least substantially of right cylindrical shape. The coil spring is arranged around the handling part. The spring arrangement is in the essentially relaxed state on pulling in the cutting loop, or has been tensioned in the pulling direction just sufficiently that it can move the fixing means with it, and is subsequently tensioned in the compression direction by the elastic force of the cutting loop in such a way that the fixing means is active. The spring arrangements satisfies a double function here in that it contracts the cutting loop and simultaneously ensures the blocking of the position that has been reached. In this way, it is possible to apply the cutting loop under an adjustable pre-stress to the organ to be cut through and to prevent slippage.

In order to be able to cut intentionally at a specific position, an instrument is provided in which the cutting loop has a metallic surface in its effective zone and is insulated elsewhere, i.e. parts of the cutting loop which are not intended to cut are of insulating design.

In order to ensure a predetermined desired loop shape after retraction of the cutting loop and subsequent extension of it a memory metal wire is preferably provided for the cutting loop.

BRIEF DESCRIPTION OF THE DRAWINGS

FIG. 3 is an axial sectional view of a high frequency surgical instrument in accordance with the invention with a single pole cutting loop of variable size, and FIG. 4 a corresponding sectional view of the instrument of FIG. 1, but enlarged relative to FIG. 1 in the region of the cutting loop and its attachment to the base part of the instrument, with the cutting loop being shown separated from the base part of the instrument.

DETAILED DESCRIPTION OF THE PREFERRED EXEMPLARY EMBODIMENTS

Figure 1:
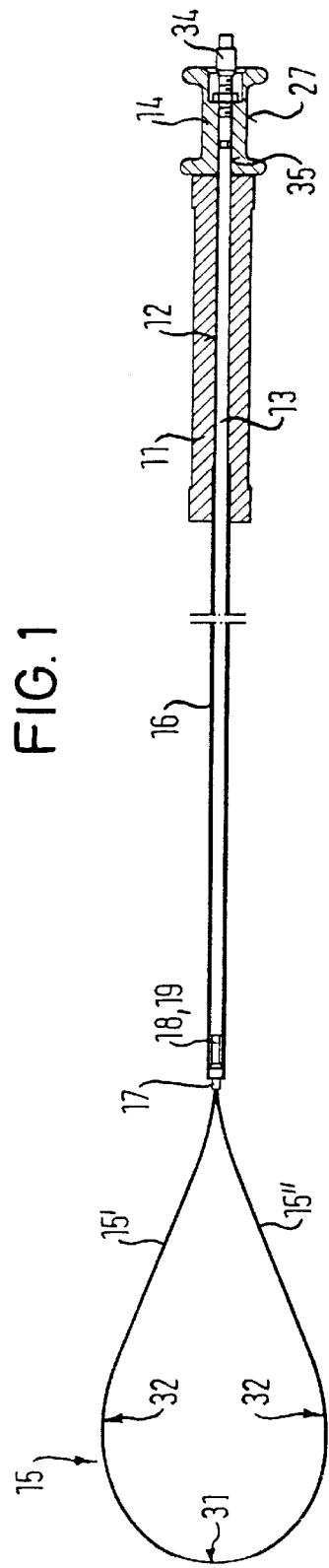
FIG. 1 is a partly sectioned side view of a first simple embodiment of a high frequency surgical instrument in accordance with the invention in the position in which the cutting loop is extended furthest.

In accordance with FIG. 1 a high frequency surgical instrument in accordance with the invention has a right cylindrical handling part 11 with a central guide channel 12 which extends through it from the front to the rear. A tube 16 is inserted into the front end region of the handling part 11 so that the guide channel 12 and the inner space of the tube 16 merge in a flush manner into one another and have at least substantially the same cross-section.

In the guide channel 12 and the tube 16, there is located a shaft 13 which is axially displaceable in the guide channel 12 and in the tube 16. A fitting or base 17 is releasably secured to the front end of the shaft 13 via a threaded connection 18, 19 which will be later described in detail with reference to FIG. 4 and the base is dimensioned, in just the same way as the threaded connection 18, 19, so that it has space within the tube 16 and is axially displaceable within this tube and optionally within the guide channel 12.

Figure 2:
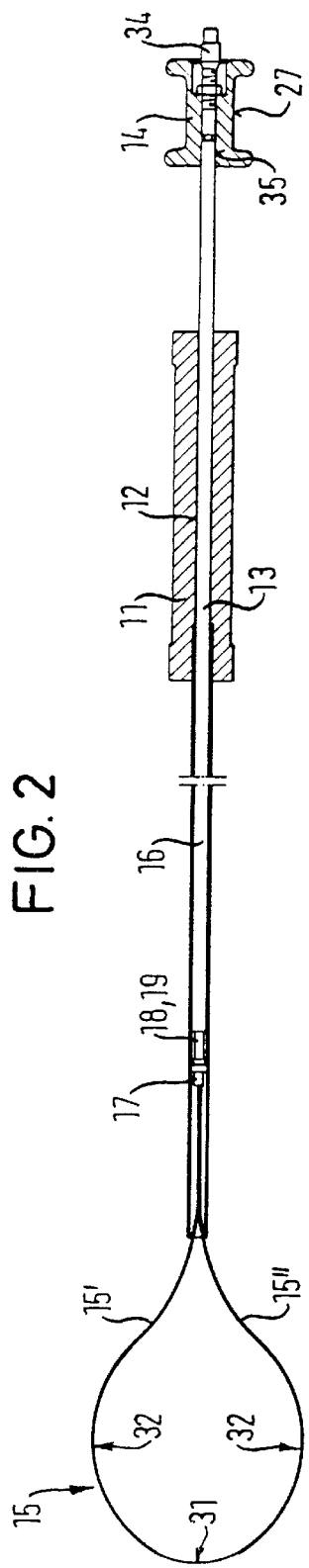
FIG. 2 is a corresponding partly sectioned side view with a partly drawn in cutting loop.

The two limbs 15', 15" of a cutting loop 15 are secured in the base 17 which projects to a greater or lesser degree out of the front end of the tube 16, depending on how far the base 16 is drawn into the tube 16 (FIGS. 1, 2).

The cutting loop 15 consists of an elastic wire which is exposed in a central cutting zone 31 and is provided in its other regions with an insulation 32.

At the rear end, the shaft 13 projects out of the rear end of the guide channel 12 and enters there into a central bore 35 of an actuating part 14 which, in the embodiment of FIGS. 1 and 2, has essentially the shape of a right cylinder with flanges at both ends, whereby a handling depression 27 extending around it is formed.

Within the actuating part 14 the shaft 13 is electrically conductively connected to a high frequency contact 34 which is preferably formed as a plug contact and which projects rearwardly and can be connected there via a suitable plugged on counterpiece to a high frequency generator.

The operation of the described instrument is as follows:

Providing the actuating part 14 is pushed sufficiently far forwardly in accordance with FIG. 1 that it contacts the rear end of the handling part 11, then the base 17 projects slightly beyond the front end of the tube 16 and the cutting loop 15 adopts its largest shape.

As soon as the cutting loop 15 has been placed around a specific tissue region during an electro-surgical operation the surgeon draws the actuating part 14 out of the position of FIG. 1 backwardly relative to the handling part 11, and indeed, for example, into the position of FIG. 2, where the two limbs 15', 15" are partly drawn into the tube 16 and the remainder of the cutting loop surrounds a substantially smaller cross-section. In this manner the tissue engaged by the cutting loop 15 can be clamped and can be ideally cut subsequently by the application of a high frequency voltage to the cutting loop 15.

After an operation the actuating part 14 can be pushed forwardly again, whereby the cutting loop 15 can be freed relatively simply from the tissue again.

In accordance with FIG. 3 a further embodiment of the high frequency surgical instrument of the invention has a handling part 11 of substantially right cylindrical shape which is terminated at the rear end by a thumb engagement ring 24 and has a central guide channel 12 which is of substantially right cylindrical shape and is open towards the front. A sleeve nut 25 adjoins the front end of the guide channel 12 remote from the thumb engagement ring 24, is screwed onto a front threaded stub 26 of the handling part 11 and carries a tube 16 which projects forwardly. The handling part 11 and the tube 16 should consist of insulating material.

On the rear right cylindrical portion of the handling part 11 there is located a ring-like actuating part 14 which is axially displaceably arranged on the handling part 11 and has a handling depression 27 for the fingers of an operator.

A metallic shaft 13 is located within the guide channel 12 and the sleeve nut 25 of the tube 16 and is preferably connected in form-fitted manner at the rear end to the actuating part 14 through a non-illustrated slot or slots in the handling part 11.

A high frequency line 28 which is only indicated also extends radially through the actuating part 14, which is preferably of insulating design, is connected to a non-illustrated high frequency generator and produces a high frequency connection from the latter to the rear end of the metal shaft 13.

An axially extending latch tooth arrangement 23 is provided in the front region of the handling part 11 at the outer side and co-operates with a locking pawl 22 which is pivotable about the transverse axis 29 on a fixing ring 21 which is axially displaceably seated on the handling part 11, with the locking pawl being arranged so that it is biased by a latch spring 30 onto the latch tooth arrangement 23. The latch lever 22 has a front latch arm 22' and a rear actuating arm 22".

The front end of the shaft 13 is provided in accordance with FIG. 4 with a spigot 19' of reduced diameter which has an outer thread 19.

In accordance with FIGS. 3 and 4, a threaded sleeve 17' provided with an inner thread 18 is screwed onto, or can be screwed onto, the threaded spigot 19' and forms the rear part of a base or socket 17 which is of substantially right cylindrical shape at which the two limbs 15', 15" of an elastic cutting loop 15 are led together and fixed in the manner which can be seen from the drawing.

The cutting loop 15 comprises an elastic wire which is outwardly exposed in the center 31 and is provided with insulation at 32.

A coil spring 20 is located on the actuating part 11 between the fixing ring 21 and the actuating ring 14.

The operation of the second embodiment of the high frequency surgical instrument of FIGS. 3 and 4 is as follows:

For the installing of a cutting loop 15 provided with a base 17 the shaft 13 is shifted sufficiently far forwardly, while releasing the latch lever 22 from the toothed latch arrangement 23, until the threaded spigot 19' on the tube 16 projects forwardly. The base 17 with the cutting loop 15 can now be screwed without problem onto the threaded spigot 19'.

Thereafter, the cutting loop 15 with the base 17 can be partly drawn into the tube 16 to a greater or lesser degree by retraction of the actuating ring 14 rearwardly on the handling part 11. The outer diameter of the base 17 is at no point greater than would permit the retraction into the internal space of the tube 16.

As soon as the base 17 is located within the tube 16, the limbs 15', 15" of the wire loop 15 come into contact with the front edge 33 (FIG. 2) of the tube 16 which leads to the surface F of the inner space of the cutting loop 15 being increasingly reduced, the further the base 17 is drawn into the tube 16. This movement is executed by the operator in that his thumb is located inside the thumb engagement ring 24 and the index and middle finger are located in the handling depression 27 of the actuating ring 14.

During this movement, the fixing ring 21 is moved at the same time via the coil spring 20, which is lightly loaded in tension, and the latch lever 23, or the latch arm 22' thereby automatically jumps from one tooth of the latch toothed arrangement 23 into the next tooth until the desired reduction of the area F of the cutting loop 15 has been achieved.

If the surgeon now releases the actuating ring 14, the elastic cutting loop 15 attempts to become broader and thereby pulls the actuating ring 14 slightly towards the front. In this way, the fixing ring 21 is moved with it until the latch arm 22 has latched into the tooth gap in the region of which it is located. As soon as the elastic draw-out force of the cutting loop 15 and the resetting force of the coil spring 20 are in balance, the size of the inner area of the cutting loop 15 which has been obtained is maintained, so that the surgeon can temporarily release the instrument and dedicate himself to other activities. At that point a further movement of the bar 13 to the front is only possible by overcoming the force of the spring 20.

If now the cutting loop is to be made large again then the surgeon only needs to press downwardly on the actuating arm 22" of the latch lever 22, whereupon the latch arm 22' disengages from the tooth latch arrangement 23 and the total arrangement comprising the actuating ring 14, the coil spring 20 and the fixing ring 21 can now be shifted forwardly, with the bar 13 moving the cutting loop 15 more and more out of the tube 16 until finally the position of FIG. 3 is reached in which it projects forwardly by the maximum amount.

I claim:

1. A high frequency surgical instrument comprising a handling part that has a guide channel that is open at at least one end and a holding element that is axially displaceably guided therein and on which a high frequency voltage acts, with the holding element being axially displaceable by means of an actuating part axially displaceable with respect to the handling part and being electrically conductively connected at its free connecting end to a preferably elastic cutting loop in such a way that, through axial adjustment of the actuating part, the cutting loop can be drawn to a varying degree into the guide channel, or into a tube which continues it outwardly, or can be pushed out of the guide channel, or out of the tube continuing it outwardly, whereby the loop size can be changed, wherein the two of the cutting loop are led to a common base which is in turn releasably connectable to a shaft that is guided in the guide channel or tube and forms the holding element and is so dimensioned that it is displaceable with the shaft within at least one of the guide channel and the tube, and wherein the shaft can be displaced forwardly in at least one of the guide channel and the tube to such an extent that its front connecting end is located adjacent to the front end of the guide channel or tube, respectively, such that the base can be either released from the connection end or connected to it.

2. An instrument in accordance with claim 1 such that the front connecting end projects out of the front end of the guide channel or tube, respectively.

3. An instrument in accordance with claim 1, wherein the base is releasably connected to the shaft via a threaded connection.

4. An instrument in accordance with claim 1, wherein the base is connectable to the shaft via a bayonet connection.

5. An instrument in accordance with claim 1, wherein the actuating part is arranged behind the handling part.

6. An instrument in accordance with claim 1, wherein the guide channel passes up to the rear end of the handling part and the shaft extends through the rear end of the guide channel to the actuating part and is fixedly connected to the actuating part.

7. An instrument in accordance with claim 1, wherein the shaft extends into the actuating part and is electrically conductively connected from there to a high frequency contact, in particular to a high frequency plug contact which can be connected from the outside to a counterpiece coming from the high frequency generator.

8. An instrument in accordance with claim 1, wherein the actuating part contacts the rear end of the handling part when the cutting loop is open to the greatest degree.

9. An instrument in accordance with claim 1, wherein the actuating part is formed as an actuating ring which is axially slidably arranged on the handling part and is connected through an elongate slot to the shaft which is axially guided inside of the handling part.

10. An instrument in accordance with claim 1, wherein the actuating part has a gripping depression which preferably extends around it.

11. An instrument in accordance with claim 1, wherein the actuating part is biased by a spring arrangement in the direction of a reduction of the loop.

12. An instrument in accordance with claim 1, wherein a fixing means is provided for the cutting loop when drawn into a specific position.

13. An instrument in accordance with claim 12, wherein the fixing means comprises a fixing device which blocks at one side and which is correspondingly co-displaced on reduction of the size of the cutting loop but is only displaceable in the sense of an increase in the size of a cutting loop through a hand actuated deblocking device.

14. An instrument in accordance with claim 12, wherein the spring arrangement is disposed between the fixing means and the actuating part.

15. An instrument in accordance with claim 13, wherein the fixing means comprises a fixing ring which is displaceably guided on the handling part and which is loaded by a spring in the blocking direction, a latch pawl arranged on the fixation and an axial latch tooth arrangement on the handling part.

16. An instrument in accordance with claim 15, wherein a coil spring is arranged between the fixing ring and the actuating part.

17. An instrument in accordance with claim 1 wherein the handling part is at least substantially of right cylindrical shape.

18. An instrument in accordance with claim 16, wherein the coil spring is arranged around the handling part.

19. An instrument in accordance with claim 11, further comprising fixing means, wherein the spring arrangement is in the essentially relaxed state on pulling in the cutting loop, or has been tensioned in the pulling direction just sufficiently that it can move the fixing means with it, and is subsequently tensioned in the compression direction by the elastic force of the cutting loop in such a way that the fixing means is active.

20. An instrument in accordance with claim 1, wherein the cutting loop has a metallic surface in its effective zone and is insulated elsewhere.

21. An instrument in accordance with claim 1 wherein the cutting loop consists at least in part and preferably fully of a memory metal wire.

* * * * *